United States Patent
Den Hartog et al.

(10) Patent No.: US 6,281,216 B1
(45) Date of Patent: Aug. 28, 2001

(54) 2-AMINOQUINOLINE DERIVATIVES HAVING D4-AGONISTIC ACTIVITY

(75) Inventors: Jacobus A. J. Den Hartog; Gerben M. Visser; Bartholomeus J. Van Steen; Martinus T. M. Tulp; Eric Ronken; Cornelis G. Kruse, all of Weesp (NL)

(73) Assignee: Duphar International Research B.V. (NL)

( * ) Notice: Subject to any disclaimer, the term of this patent is extended or adjusted under 35 U.S.C. 154(b) by 0 days.

(21) Appl. No.: 09/601,765
(22) PCT Filed: Jan. 5, 1999
(86) PCT No.: PCT/EP99/00855
§ 371 Date: Oct. 23, 2000
§ 102(e) Date: Oct. 23, 2000
(87) PCT Pub. No.: WO99/40068
PCT Pub. Date: Aug. 12, 1999

(30) Foreign Application Priority Data

Feb. 9, 1998 (EP) .................................................. 98200399

(51) Int. Cl.$^7$ ...................... A61K 31/496; C07D 401/12; A61P 25/00
(52) U.S. Cl. .................... 514/253.06; 514/313; 544/363; 544/405; 546/163
(58) Field of Search ................................... 544/363, 405; 514/253.06, 313; 546/163

(56) References Cited

U.S. PATENT DOCUMENTS 5,093,333   3/1992   Saab .................................. 514/235.2

FOREIGN PATENT DOCUMENTS 0 512 755 A2   11/1992   (EP) .
0 745 598 A1   12/1996   (EP) .

*Primary Examiner*—Deborah C. Lambkin
*Assistant Examiner*—Andrea M. D'Souza
(74) *Attorney, Agent, or Firm*—Finnegan, Henderson, Farabow, Garrett & Dunner, L.L.P.

(57) ABSTRACT

The present invention relates to a group of novel 2-aminoquinoline derivatives which are potent and selective agonists of the dopamine D4-receptor. The compounds have general formula (I) wherein $(R_1)_n$ represents 1 or 2 substituents, which can be the same or different, from the group $C_{1-3}$-alkyl or alkoxy, halogen, trifluoromethyl, nitro, amino, and mono- or dialkyl $(C_{1-2})$amino, or two groups $R_1$ at adjacent carbon atoms together with the benzene ring may form the benzdioxane group or benzofuran group, X represents nitrogen or carbon, and the dotted line may represent a double bond, $(R_2)_p$ represents 0, 1 or 2 substituents, which can be the same or different, from the group methyl and ethyl, or $(R_2)_p$ is a methylene bridge or ethylene bridge, $R_3$ is hydrogen or methyl, and $(R)_m$ represents 0, 1, or 2 substituents, which can be the same or different and can be located at all available positions of the quinolyl group, from the group $C_{1-3}$-alkyl or alkoxy, halogen, trifluoromethyl, nitro, amino, and mono- or dialkyl $(C_{1-2})$amino, on the understanding that $R_1$ cannot represent o-OCH$_3$ when X is nitrogen, $(R_2)_p$ and $R_3$ are hydrogen, m is 0 and n is 1

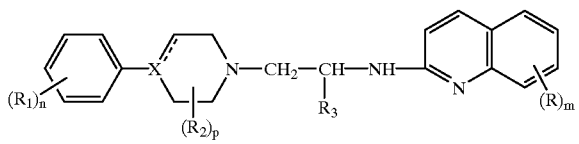

(I)

18 Claims, No Drawings

2-AMINOQUINOLINE DERIVATIVES HAVING D4-AGONISTIC ACTIVITY

This application is a 371 of PCT/EP99/00855 Jan. 5, 1999.

The present invention relates to a group of novel 2-aminoquinoline derivatives, to a method for the preparation of these compounds, and to pharmaceutical compositions containing one or more of these compounds as an active component.

It has surprisingly been found that the compounds and salts thereof of the formula (I)

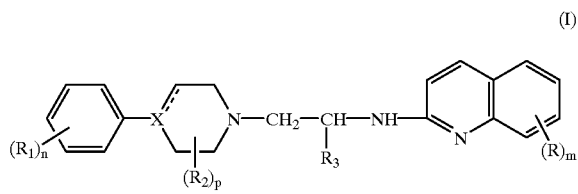

wherein
$(R_1)_n$ represents 1 or 2 substituents, which can be the same or different, from the group $C_{1-3}$-alkyl or alkoxy, halogen, trifluoromethyl, nitro, amino, and mono or dialkyl ($C_{1-2}$) amino, or two groups $R_1$ at adjacent carbon atoms together with the benzene ring may form the benzdioxane group or benzofuran group,
X represents nitrogen or carbon, and the dotted line may represent a double bond,
$(R_2)_p$ represents 0, 1 or 2 substituents, which can be the same or different, from the group methyl and ethyl, or $(R_2)_p$ is a methylene bridge or ethylene bridge,
$R_3$ is hydrogen or methyl, and
$(R)_m$ represents 0, 1 or 2 substituents, which can be the same or different and can be located at all available positions of the quinolyl group, from the group $C_{1-3}$-alkyl or akoxy, halogen, trifluoromethyl, nitro, amino, and mono- or dialkyl ($C_{1-2}$)-amino,
on the understanding that $R_1$ cannot represent o-$OCH_3$ when X is nitrogen, $(R_2)_p$ and $R_3$ are hydrogen, and m is 0 and n is 1,
are potent and selective agonists of the dopamine D4-receptor.

Compounds having formula (I) wherein R, $R_1$ and X have the above meaning, m is 0 or 1, n is 1, and $(R_2)_p$ and $R_3$ represent hydrogen, and salts thereof are preferred.

Especially preferred are compounds having formula (I) wherein R, $R_1$, X, m, n, $(R_2)_p$ and $R_3$ have the meanings given in claim 2 and salts thereof.

Of particular interest is the compound 1-(2-[2-quinolyl]amino)-ethyl-4-(4-methoxyphenyl) piperazine, and salts thereof.

Due to the potent and selective D4-agonistic activity the compounds according to the invention are suitable for use in the treatment of psychiatric disorders such as psychosis, anxiety, depression, attention deficits, memory disorders, neurological disorders such as Parkinson's disease and ischaemia and other CNS-diseases involving dopaminergic neurotransmission.

The affinity of the compounds of the invention for dopamine D4 receptors was determined using CHO-K1 cells which are stably transfected to express the human recombinant dopamine receptor, D4.2 subtype (Van Tol et al, Nature 350, 610, 1991) and using [3H]-Spiperone as the ligand. After incubation of a freshly prepared cellmembrane preparation with the [3H]-ligand, with or without addition of compounds of the invention, separation of bound and free ligand was performed by filtration over glassfiberfilters (Research Biochemicals International protocol, Catalog No. D-177). Radioactivity on the filter was measured by liquid scintillation counting. Results are expressed as IC50 values and transformed into inhibitory constants (Ki).

The dopamine D4 agonistic activity of compounds of the invention was determined by functional studies using CHO-K1 cells stably expressing the human dopamine D4.4 receptor (Van Tol, et al, Nature, 358, 149, 1992). These cells were fitted with a construct encoding a truncated form of alkaline phosphatase, causing it to get secreted by the cells. Expression of this secretable alkaline phosphatase (SeAP) is under direct control of cellular cyclic AMP (Berger et al, Gene, 66, 1, 1988). SeAP measurements were done with p-nitrophenylphosphate (pNPP) as the substrate using colorimetric readout at 450 nm. Dopamine D4 agonist activity was determined by incubation of cells with prostaglandin PGE1 (1 uM), with or without addition of compounds of the invention, and subsequent quantification of the concentration-dependant attenuation of dopamine D4 receptor mediated SeAP formation, yielding estimates of intrinsic activity and potency (pEC50 values). Quinpirole and dopamine were used as reference dopamine agonists.

Absence of dopamine D4 antagonistic activity was confirmed using the same assay, but co-incubating cells with prostaglandin PGE1 (1 uM) and the standard agonist quinpirole (1 uM), with or without addition of compounds of the invention. In this way, the antagonistic effect of compounds of the invention against agonist dependant attenuation of dopamine D4 receptor mediated stimulation of adenylate cyclase and subsequent SeAP formation was determined.

Dopamine D4 agonist properties and the absence of D4 antagonist properties of selected compounds of the invention were further confirmed using radioactive measurements of cAMP formation according to Salomon et al. (Anal Biochem, 58, 541, 1974) as modified by Weiss et al. (J Neurochem 45, 869, 1985).

The selectivity of the compounds of the invention with regard to the dopamine D2 receptor, was determined by measuring the affinity for dopamine D2 receptors using rat brain homogenates and [3H]-Spiperone as the ligand (Leysen et al, Biochem Pharmacol 27, 307, 1978). After incubation of a freshly prepared cellmembrane preparation with the [3H]-ligand, with or without addition of compounds of the invention, separation of bound and free ligand was performed by filtration over glassfiberfilters. Radioactivity on the filter was measured by liquid scintillation counting. Results are expressed as IC50 values and transformed into inhibitory constants (Ki).

The dopamine D2 (ant)agonistic activity of compounds of the invention was determined by functional studies based on radioactive measurements of cAMP formation according to Salomon et al. (Anal Biochem, 58,541, 1974) as modified by Weiss et al. (J Neurochem 45, 869, 1985), using CHO cells, stably expressing human dopamine D2L receptors (Grandy et al, Proc Natl Acad Sci USA, 86, 9762, 1989).

Suitable acids with which the compounds can form pharmaceutically acceptable acid addition salts are for example hydrochloric acid, sulphuric acid, phosphoric acid, nitric acid, and organic acids such as citric acid, fumaric acid, maleic acid, tartaric acid, acetic acid, benzoic acid, p-toluene sulphonic acid, methane sulphonic acid and naphthalene sulphonic acid.

The compounds of the invention can be brought into forms suitable for administration by means of usual processes using auxiliary substances and/or liquid or solid carrier materials.

The compounds of the invention having formula (I) can be obtained according to methods known for the synthesis of structurally related compounds.

A suitable method for the preparation of the compounds having formula (I) is the following:

Step 1
Reaction of a compound having formula (II):

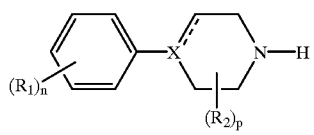

with chloroacetonitrile in a polar solvent such as acetonitrile in the presence of a base such as triethylamine.

Step 2
The obtained N-cyanomethyl derivative of the compound of formula (II) can be hydrogenated with a reducing agent such as lithium aluminium hydride in an aprotic solvent such as tetrahydrofuran to give the corresponding 2-aminoethyl derivative having formula (III):

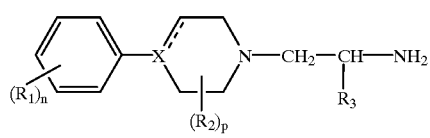

Step 3:
The compound having formula (III) is then reacted with a suitable 2-chloroquinoline derivative of the formula (IV):

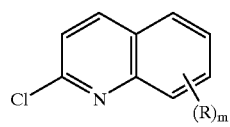

in the presence of a base such as potassium carbonate in a polar aprotic solvent such as dimethylsulfoxide at 20–140° C., to give the desired compound having formula (I).

The preparation of the compounds of the present invention is illustrated with the following examples.

EXAMPLE I
1-(2-[2-quinolyl]amino)-ethyl-4-(4-methoxyphenyl) piperazine.hydrochloride Part A:
To a solution of 19.2 g (100 mmol) of commercially available 4-methoxyphenyl piperazine in acetonitrile (300 ml), 12.1 g (120 mmol) of triethylamine and 7.6 g (100 mmol) of chloroacetonitrile were subsequently added. The reaction mixture was refluxed for 2 hrs, cooled to room temperature and concentrated in vacuo. To the residue dichloromethane (300 ml) and water (150 ml) were added, the water layer was further extracted with dichloromethane (50 ml), the combined organic layers were dried over sodiumsulphate and concentrated in vacuo. In this manner 18.5 g of 1-(cyanomethyl)-4-(4-methoxyphenyl) piperazine (80%) was obtained as a white solid.

Part B:
To a solution of 18.5 g (80 mmol) of 1-(cyanomethyl)-4-(4-methoxyphenyl) piperazine in dry tetrahydrofuran (350 ml), heated to 40° C., a quantity of 6.1 g (160 mmol, 2 equivalent) of lithium aluminium hydride was added in portions. Cooling of the reaction mixture was required to keep the temperature at about 40° C. during addition of the lithium aluminium hydride. After reflux for 1 hr. the mixture was cooled to room temperature and subsequent dropwise addition was carried out of 1). a mixture of water (6 ml) and tetrahydrofuran (40 ml), 2). a solution of sodium hydroxide in water (2N, 12 ml) and 3). water (12 ml). The reaction mixture was heated at 40° C. for 2 hrs. The precipitate obtained after cooling to room temperature was removed by filtration and washed with tetrahydrofuran (two times 25 ml). The filtrate was concentrated in vacuo. To the filtrate water (300 ml) and dichloromethane (150 ml) were added, the water layer was further extracted with dichloromethane (two times 100 ml), the combined organic layers were dried over sodium sulphate and concentrated in vacuo. The product was purified applying flash-chromatography over silicagel using dichloromethane/methanol/ammonia 85:14:1 as the eluent. After concentration in vacuo a total of 9.4 g of 1-(2-aminoethyl)-4-(4-methoxyphenyl) piperazine (50% yield) was obtained as an oil, slowly solidifying at room temperature.

Part C:
A solution of 9.4 g (40 mmol) of 1-(2-aminoethyl)-4-(4-methoxyphenyl) piperazine in dry dimethyl sulfoxide (30 ml), 6.5 g (40 mmol) of commercially available 2-chloroquinoline and 6.1 g (44 mmol, 1.1 equivalent) of dry potassium carbonate were heated to 120° C. under nitrogen for 20 hrs. After cooling to room temperature water (150 ml) and dichloromethane (100 ml) were added. The water layer was further extracted with dichloromethane (two times 100 ml), the combined organic layers were washed with water (40 ml), dried over sodium sulphate and concentrated in vacuo. The product was purified applying flash-chromatography over silicagel using dichloromethane/methanol 95:5 as the eluent. After concentration in vacuo the residual oil was dissolved in absolute ethanol (80 ml), heated to 70° C. and a solution of 1.46 g hydrochloride (40 mmol) in absolute ethanol (10 ml) was added. After stirring for ½ hr at 70° C., subsequent cooling and stirring at room temperate for 2 hrs, the resulting precipitate was collected by filtration, washed with hexane (two times 25 ml) and dried in vacuo. In this manner 10.2 g of 1-(2-[2-quinolyl]amino)-ethyl-4-(4-methoxyphenyl) piperazine.hydrochloride was obtained as a white solid (64% yield).

In an analogous manner the compounds having formula (I), wherein $R_2$ and $R_3$ are hydrogen listed below have been prepared:

TABLE

| Example | $(R)_m$ | X | $(R_1)_n$ | Salt |
|---|---|---|---|---|
| II | H | piperazine | benzofuran-7-yl | 2.fumarate |
| III | H | piperazine | 1,4-benzodioxan-5-yl | fumarate |
| IV | H | piperazine | m-$CF_3$-phenyl | 2.HCl |
| V | H | piperazine | p-Cl-phenyl | 2.HCl |
| VI | H | 3,4-dehydro-piperidine | p-$CH_3O$-phenyl | base |
| VII | H | piperidine | p-$CH_3O$-phenyl | base |
| VIII | 6-Cl | piperazine | p-$CH_3O$-phenyl | base |
| IX | 7-Cl | piperazine | p-$CH_3O$-phenyl | base |
| X | 8-Cl | piperazine | p-$CH_3O$-phenyl | base |

TABLE-continued

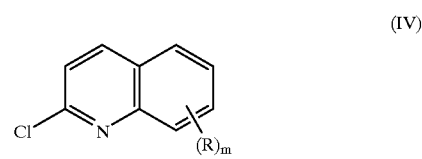

| Example | $(R)_m$ | | $(R_1)_n$ | Salt |
|---|---|---|---|---|
| XI | 4-$CH_3$ | piperazine | p-$CH_3$O-phenyl | base |
| XII | 8-$OCH_3$ | piperazine | p-$CH_3$O-phenyl | base |
| XIII | 5-Cl | piperazine | p-$CH_3$O-phenyl | base |

What is claimed is:

1. A compound of formula (I) or a salt thereof

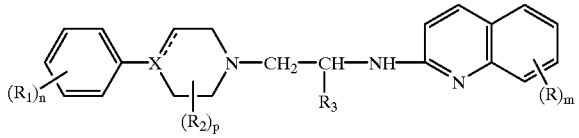

(I)

wherein $(R_1)_n$ represents 1 or 2 substituents, which substituents can be the same or different, and are chosen from $C_{1-3}$-alkyl, $C_{1-3}$-alkoxy, halogen, trifluoromethyl, nitro, amino, monoalkyl $(C_{1-2})$-amino, and dialkyl $(C_{1-2})$-amino groups, or two $R_1$ groups at adjacent carbon atoms, together with the benzene ring to which they are attached, form a benzdioxane group or a benzofuran group, X represents nitrogen or carbon, wherein if X is carbon, the dotted line represents a double bond, $(R_2)_p$ represents 0, 1 or 2 substituents, which substituents can be the same or different, and are chosen from methyl and ethyl groups, or $(R_2)_p$ is a methylene bridge or an ethylene bridge, $R_3$ is hydrogen or a methyl group, and $(R)_m$ represents 0, 1 or 2 substituents, which substituents can be the same or different and can be located at any available position of the quinolyl group, and which substituents are chosen from $C_{1-3}$-alkyl, $C_{1-3}$-akoxy, halogen, trifluoromethyl, nitro, amino, monoalkyl $(C_{1-2})$-amino, and dialkyl $(C_{1-2})$-amino groups, provided that $R_1$ does not represent o-$OCH_3$ when X is nitrogen, $(R_2)_p$ and $R_3$ are hydrogen, m is 0 and n is 1.

2. The compound according to claim 1, wherein $(R_2)_p$ and $R_3$ are hydrogen, m is 0 or 1, and n is 1, or a salt thereof.

3. The compound according to claim 1, wherein $(R_1)_n$ is p-$OCH_3$, or a salt thereof.

4. The compound 1-(2-[2-quinolyl]amino)ethyl-4-(4-methoxyphenyl) piperazine or a salt thereof.

5. A method for preparing a compound of formula (I) or a salt thereof according to claim 1, said method comprising reacting a compound of formula (III)

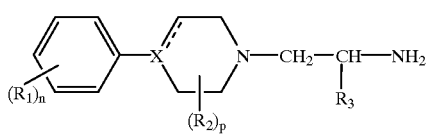

(III)

with a compound of formula (IV)

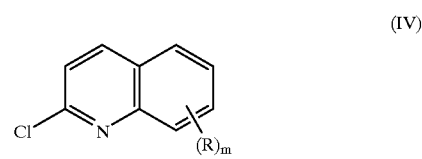

(IV)

wherein $(R_1)_n$, $(R_2)_p$, X, and $(R)_m$ are defined as in claim 1.

6. The method according to claim 5, wherein said reaction occurs in the presence of a base and a polar aprotic solvent.

7. The method according to claim 6, wherein said base is potassium carbonate and said polar aprotic solvent is dimethylsulfoxide.

8. The method according to claim 5, wherein said reaction occurs at a temperature ranging from 20 to 140° C.

9. A pharmaceutical composition, said composition comprising at least one compound of formula (I) according to claim 1, or a salt thereof, as an active component.

10. The composition according to claim 9, wherein said active component is present in an amount effective for treatment of at least one CNS disease involving dopaminergic neurotransmission.

11. The composition according to claim 9, wherein said composition further comprises a liquid or solid carrier material.

12. A method of preparing a pharmaceutical composition, said method comprising combining at least one solid or liquid carrier material with a compound of formula (I) according to claim 1, or a salt thereof, as an active component.

13. The method according to claim 12, wherein said active component is present in an amount effective for treatment of at least one CNS disease involving dopaminergic neurotransmission.

14. A method for treating at least CNS disease, said method comprising administering to a host in need of said treatment an effective amount of at least one compound of formula (I) according to claim 1, or a salt thereof, wherein said CNS disease involves dopaminergic neurotransmission.

15. The method according to claim 14, wherein said CNS disease comprises a psychiatric disorder.

16. The method according to claim 15, where said psychiatric disorder comprises at least one disorder chosen from a psychosis, anxiety, depression, an attention deficit disorder and a memory disorder.

17. A method according to claim 16, wherein said CNS disease comprises a neurological disorder.

18. The method according to claim 17, where said neurological disorder comprises at least one disorder chosen from Parkinson's disease and ischaemia.

* * * * *

UNITED STATES PATENT AND TRADEMARK OFFICE
CERTIFICATE OF CORRECTION

PATENT NO. : 6,281,216 B1
DATED : August 28, 2001
INVENTOR(S) : Den Hartog et al.

It is certified that error appears in the above-identified patent and that said Letters Patent is hereby corrected as shown below:

Title page,
Item [57], ABSTRACT,
Line 7, "$(C_{1-2})$amino" should read -- $(C_{1-2})$-amino --.
Line 18, "$(C_{1-2})$amino" should read -- $(C_{1-2})$-amino --.
Line 20, after "n is 1", insert a period.

Column 5, claim 1,
Line 45, $C_{1-3}$-akoxy" should read -- $C_{1-3}$-alkoxy --.

Signed and Sealed this

Ninth Day of April, 2002

Attest:

JAMES E. ROGAN
*Director of the United States Patent and Trademark Office*

*Attesting Officer*